United States Patent
Morlet

(10) Patent No.: US 9,867,736 B2
(45) Date of Patent: Jan. 16, 2018

(54) NEEDLE TIP FOR SURGICAL INSTRUMENT

(76) Inventor: Nigel Morlet, Mosman Park (AU)

(*) Notice: Subject to any disclaimer, the term of this patent is extended or adjusted under 35 U.S.C. 154(b) by 416 days.

(21) Appl. No.: 13/638,204

(22) PCT Filed: Mar. 28, 2011

(86) PCT No.: PCT/AU2011/000352
§ 371 (c)(1),
(2), (4) Date: Sep. 28, 2012

(87) PCT Pub. No.: WO2011/120080
PCT Pub. Date: Oct. 6, 2011

(65) Prior Publication Data
US 2013/0023918 A1    Jan. 24, 2013

(30) Foreign Application Priority Data

Mar. 29, 2010   (AU) .................... 2010901302

(51) Int. Cl.
*A61B 17/32*   (2006.01)
*A61F 9/007*   (2006.01)

(52) U.S. Cl.
CPC ..... *A61F 9/00745* (2013.01); *A61B 2017/32008* (2013.01); *A61B 2017/320072* (2013.01); *A61B 2017/320096* (2013.01)

(58) Field of Classification Search
CPC ............. A61F 9/00736; A61F 9/00745; A61F 9/00754; A61F 9/00763;
(Continued)

(56) References Cited

U.S. PATENT DOCUMENTS 1,333,745 A * 3/1920 Wescott .................... 452/69
2,711,733 A    8/1951 Jacoby, Jr.
(Continued)

FOREIGN PATENT DOCUMENTS

DE   196 28 252   1/1998
DE   199 42 693   3/2001
(Continued)

OTHER PUBLICATIONS

International-Type Search Report issued in National Application No. 2008904517, dated Oct. 27, 2008—2 pages.
(Continued)

*Primary Examiner* — Ryan J Severson
*Assistant Examiner* — Christian Knauss
(74) *Attorney, Agent, or Firm* — Hamre, Schumann, Mueller & Larson, P.C.

(57) ABSTRACT

A needle 10 for a surgical instrument for removal of diseased or unwanted tissue comprises a hollow elongate needle shaft 12 having a needle tip 14 for cutting tissue at a distal end of the needle shaft 12. The needle tip 14 is flared in at least one plane and has a flattened posterior lip 16 and a curved anterior lip 18 to produce a substantially D-shaped tip mouth 20 in a plane that is substantially orthogonal to a central longitudinal axis C—O—C' (the needle axis) of the needle 10. A major axis A-A' of the tip mouth 20 is larger than an outer diameter of the needle shaft 12 and a minor axis B—B' is smaller than the major axis A-A'. The asymmetry of the tip mouth provides improved cutting action during phacoemulsification.

24 Claims, 3 Drawing Sheets

(58) Field of Classification Search
CPC ........ A61F 2017/320072; A61F 2017/320076;
A61F 17/06066; A61F 17/062; A61F
17/34; A61F 17/3417
USPC .................................. 604/22; 606/166, 223
See application file for complete search history.

(56) References Cited

U.S. PATENT DOCUMENTS

| | | | |
|---|---|---|---|
| 2,828,744 A * | 4/1958 | Hirsch et al. ............ 604/165.01 |
| 2,904,045 A * | 9/1959 | Owings ........................ 604/274 |
| 3,071,135 A | 1/1963 | Baldwin et al. |
| 3,173,200 A | 3/1965 | Dunmire et al. |
| 3,589,363 A | 6/1971 | Banko |
| 3,633,580 A * | 1/1972 | Knox ............................ 604/274 |
| 3,788,320 A * | 1/1974 | Dye ........................ 604/165.04 |
| 4,061,146 A * | 12/1977 | Baehr et al. .................. 606/107 |
| 4,490,139 A | 12/1984 | Huizenga et al. |
| 4,561,445 A | 12/1985 | Berke et al. |
| 4,689,040 A | 8/1987 | Thompson |
| 4,889,529 A | 12/1989 | Haindl |
| 4,959,049 A | 9/1990 | Smirmaul |
| 5,047,043 A * | 9/1991 | Kubota et al. ................ 606/169 |
| 5,162,044 A | 11/1992 | Gahn et al. |
| 5,354,537 A | 10/1994 | Moreno |
| 5,515,871 A | 5/1996 | Bittner et al. |
| 5,653,724 A | 8/1997 | Imonti |
| 5,725,495 A | 3/1998 | Strukel et al. |
| 5,733,266 A | 3/1998 | Gravlee, Jr. |
| 5,788,679 A * | 8/1998 | Gravlee, Jr. .................. 604/272 |
| 5,871,492 A * | 2/1999 | Sorensen ...................... 606/166 |
| 5,938,635 A * | 8/1999 | Kuhle .......................... 604/506 |
| 5,968,022 A | 10/1999 | Saito |
| 5,993,408 A * | 11/1999 | Zaleski .......................... 604/22 |
| 5,997,499 A | 12/1999 | Sussman et al. |
| 6,007,555 A | 12/1999 | Devine |
| 6,074,396 A * | 6/2000 | Geuder ......................... 606/107 |
| 6,159,175 A * | 12/2000 | Strukel et al. .................. 604/22 |
| 6,165,150 A * | 12/2000 | Banko ............................ 604/22 |
| 6,283,974 B1 | 9/2001 | Alexander |
| 6,299,591 B1 | 10/2001 | Banko |
| 6,398,759 B1 | 6/2002 | Sussman et al. |
| 6,533,750 B2 * | 3/2003 | Sutton et al. .................. 604/22 |
| 6,565,542 B2 * | 5/2003 | Kumar et al. ................ 604/264 |
| 7,588,553 B2 | 9/2009 | Dewey |
| D633,617 S * | 3/2011 | Bricker et al. ............... D24/150 |
| 7,947,039 B2 * | 5/2011 | Sartor ............................ 606/42 |
| 2002/0062093 A1* | 5/2002 | Soring et al. ...................... 601/2 |
| 2002/0065492 A1* | 5/2002 | McGuckin et al. .......... 604/264 |
| 2002/0099325 A1 | 7/2002 | Sutton |
| 2002/0156492 A1 | 10/2002 | Timm et al. |
| 2004/0193121 A1 | 9/2004 | Kadziauskas et al. |
| 2004/0215206 A1 | 10/2004 | Kadziauskas et al. |
| 2005/0020990 A1 | 1/2005 | Akahoshi |
| 2005/0222598 A1 | 10/2005 | Ho |
| 2006/0052758 A1 | 3/2006 | Dewey |
| 2006/0217672 A1 | 9/2006 | Chon |
| 2006/0235305 A1* | 10/2006 | Cotter et al. .................. 600/459 |
| 2006/0253056 A1 | 11/2006 | Kadziauskas et al. |
| 2007/0078378 A1* | 4/2007 | Kao et al. ........................ 604/27 |
| 2007/0213633 A1* | 9/2007 | McClellan .......... A61B 10/0266 600/564 |
| 2007/0260199 A1 | 11/2007 | Rockley |
| 2008/0058708 A1* | 3/2008 | Akahoshi ........................ 604/22 |
| 2008/0139994 A1 | 6/2008 | Mackool et al. |
| 2008/0188792 A1 | 8/2008 | Barrett |
| 2009/0099536 A1* | 4/2009 | Akahoshi ...................... 604/272 |
| 2009/0137971 A1 | 5/2009 | Akahoshi |
| 2009/0192440 A1 | 7/2009 | Akahoshi |
| 2011/0015561 A1* | 1/2011 | Akahoshi ........................ 604/22 |
| 2011/0046541 A1 | 2/2011 | Akahoshi |
| 2011/0166502 A1* | 7/2011 | Nallakrishnan ................ 604/22 |

FOREIGN PATENT DOCUMENTS

| | | |
|---|---|---|
| EP | 0 619 993 | 10/1994 |
| EP | 0 962 205 | 12/1999 |
| EP | 1 464 310 | 10/2004 |
| EP | 1 532 996 | 5/2005 |
| JP | 2006-000644 | 1/2006 |
| JP | 2008-154842 | 7/2008 |
| JP | 2008-154843 | 7/2008 |
| WO | 94/22402 | 10/1994 |
| WO | 00/74615 | 12/2000 |
| WO | 02/16059 | 2/2002 |
| WO | 2005/025434 | 3/2005 |
| WO | 2005/032439 | 4/2005 |
| WO | 2007/119107 | 10/2007 |
| WO | 2008/147771 | 12/2008 |
| WO | 2009/000959 | 12/2008 |
| WO | 2010/022460 | 3/2010 |
| WO | 2013/016772 | 2/2013 |

OTHER PUBLICATIONS

International-Type Search Report issued in National Application No. 2010901302, dated Jul. 1, 2010—2 pages.
International-Type Search Report issued in National Application No. 2010901302, dated Aug. 12, 2010—2 pages.
International Search Report issued in International Application No. PCT/AU2009/001109, dated Oct. 28, 2009—5 pages.
International-Type Search Report issued in National Application No. 2011903103, dated Jun. 7, 2012—3 pages.
International Search Report issued in International Application No. PCT/AU2011/000352, dated Jun. 17, 2011—6 pages.

* cited by examiner

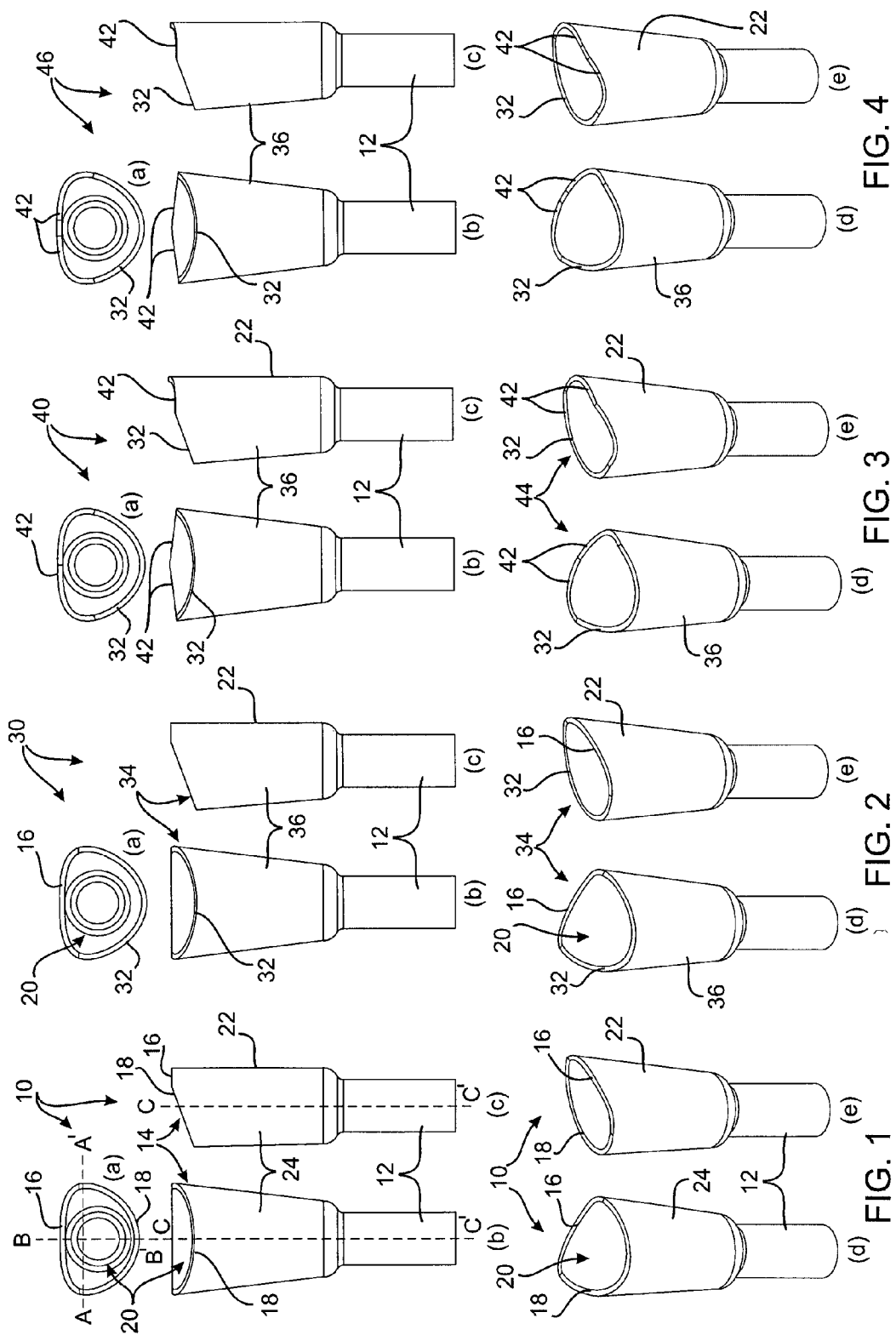

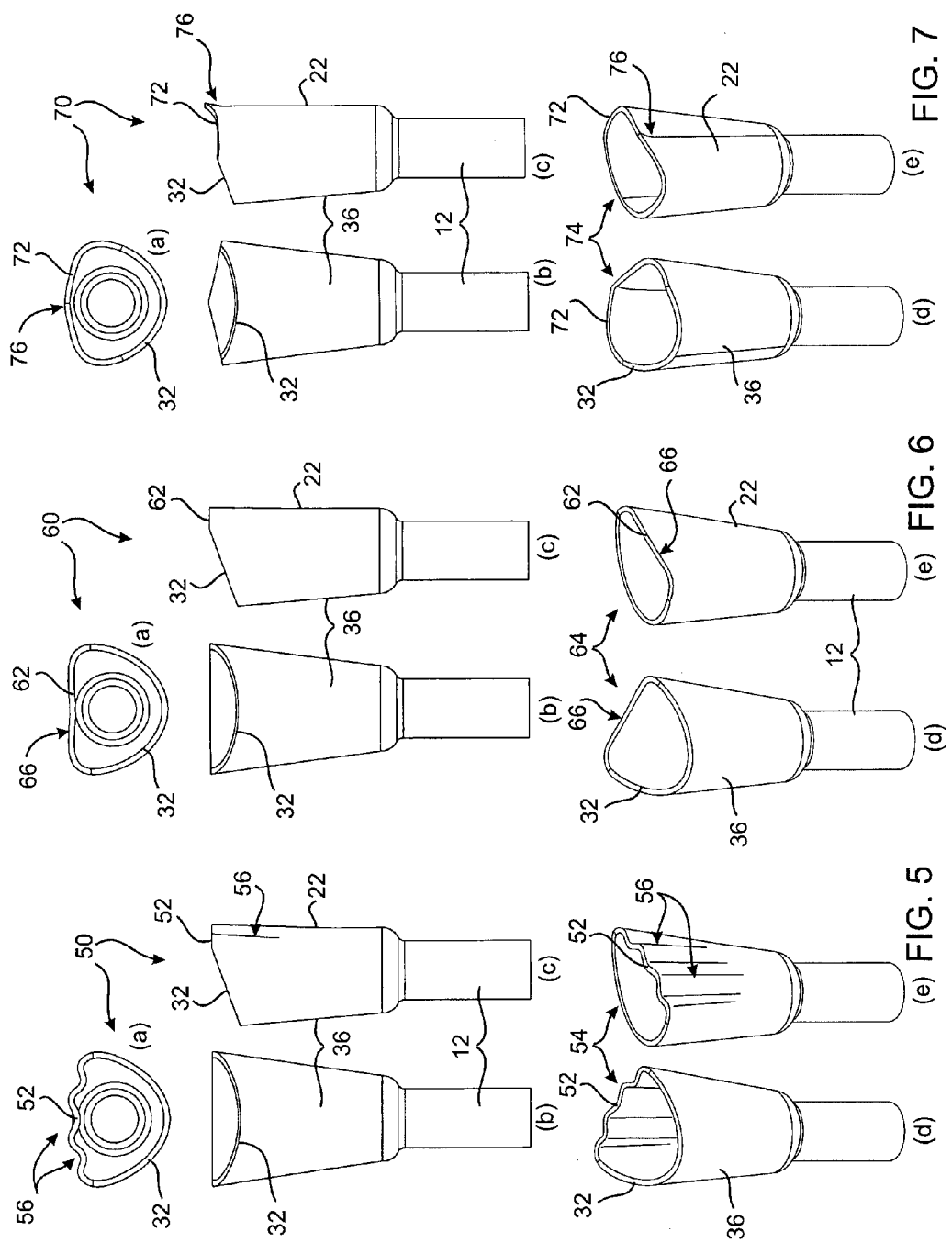

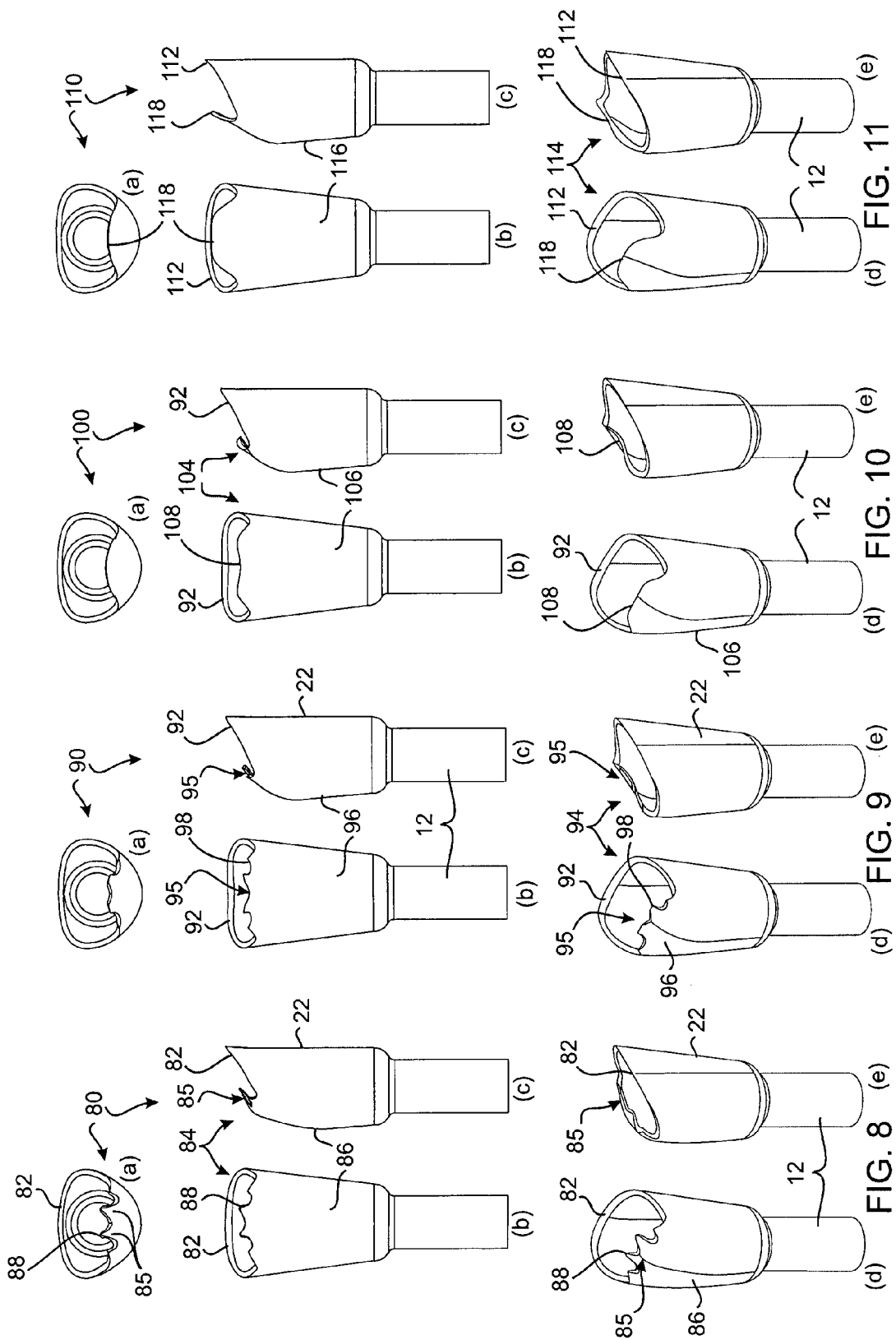

NEEDLE TIP FOR SURGICAL INSTRUMENT

FIELD OF THE INVENTION

The present invention relates to an improved needle tip for a surgical instrument and relates particularly, though not exclusively, to a needle tip for an ultrasonic surgical instrument of the kind used for phacoemulsification in surgical cataract removal procedures.

BACKGROUND TO THE INVENTION

Ophthalmologists have developed surgical cataract removal procedures which involve removal of the crystalline lens and replacement with an artificial lens through a small incision in the capsular bag in which the lens material is contained. Charles Kelman and Anton. Banko were among the first to successfully develop a technique for removal of cataracts using a handheld surgical instrument with a hollow needle vibrating at ultrasonic frequencies. U.S. Pat. No. 3,589,363 describes their ground-breaking technique. This technique, which has become known as phacoemulsification, involves inserting a needle tip vibrating at ultrasonic frequencies into the eye through a small corneal incision. As the vibrating needle tip and ultrasonic wave contacts the lens material it disintegrates and emulsifies it with an irrigating fluid. A coaxial sleeve over the needle or a second canula delivers the irrigating fluid, and the disintegrated lens disperses to form an emulsion which is aspirated through the hollow interior of the needle.

Depending on the extent of the cataract formation the diseased lens material can vary considerably in hardness and/or density. The harder or more dense the diseased material the more difficult it is to remove using phacoemulsification. Various types of ultrasonic vibration have been tried to improve the rate and, efficiency of emulsification; previously using longitudinal alone, but recently using transverse and torsional vibration, as well as combinations thereof. In addition, many have developed alternative needle and tip configurations to try to improve on the standard round needle with a bevelled tip. For example, tips that are flared to produce an "acoustic horn" to, focus the ultrasonic sound waves. Yet other examples use transverse steps or "baffles", or concave recesses within the mouth of the tip to enhance cavitation and emulsification.

The effect of these tip modifications with transverse or torsional ultrasound is limited because the designs were principally for longitudinal movement of the needle. A standard round tip on a straight needle cannot work with torsional ultrasound handpieces; the rotary tip motion produced simply "cores" out the material rather than breaking and emulsifying it. The bent needle that Kelman developed is used because it transforms the rotary needle motion into a sweeping or "scything" tip motion. However this type of bent needle has poor ergonomics and can be difficult to use during phacoemulsification surgery. Because of poor tip cutting efficiency, it is also easily blocked with incompletely emulsified lens material.

The present invention was developed to providing an improved needle tip configuration with better phacoemulsification efficiency, principally for torsional and transverse ultrasonic handpieces without compromising linear phacoemulsification. It will be appreciated that the same type of needle tip may also be used for other types of surgical procedure such as removal of tumours (e.g. brain tumours), liposuction, or in dentistry. Therefore the invention is not limited in its application to phacoemulsification.

References to prior art in this specification are provided for illustrative purposes only and are not to be taken as an admission that such prior art is part of the common general knowledge in Australia or elsewhere.

SUMMARY OF THE INVENTION

According to one aspect of the present invention there is provided a needle for a surgical instrument for removal of diseased or unwanted tissue, the needle comprising:

a hollow elongate needle shaft having a needle tip at a distal end for cutting tissue, the needle tip being flared in at least one plane and having a flattened posterior lip and an anterior lip shaped to produce an asymmetric tip mouth with a major axis larger than an outer diameter of the needle shaft and a minor axis smaller than the major axis.

Preferably the anterior lip is curved to produce a substantially D-shaped tip mouth.

Typically the flattened posterior lip is on an edge of a posterior surface that lies in a plane that is substantially parallel to a central longitudinal axis of the needle shaft. Preferably the needle tip has a central longitudinal axis (the tip axis) which is substantially parallel to the central longitudinal axis of the needle shaft. In one embodiment the anterior lip of the tip mouth is also flattened and is on the edge of an anterior surface that lies in a plane that is substantially parallel to a central longitudinal axis of the needle shaft.

Preferably the substantially D-shaped tip mouth lies in a plane that is substantially orthogonal to a central longitudinal axis (the needle axis) of the needle shaft. Advantageously the posterior lip is substantially transverse to the minor axis of the tip mouth and is on the edge of the posterior surface which is substantially parallel to the major axis of the tip mouth.

Preferably the major axis of the tip mouth is about 1.2 to 2.5 times longer than the minor axis preferably the minor axis is about 1.0 to 1.5 times the diameter of the needle shaft.

Preferably at least a portion of the lip of the tip mouth is cut or chamfered at an angle with respect to the tip axis. Preferably at least a portion of the lip of the tip mouth is chamfered in a plane that is substantially parallel to the major axis of the tip mouth. Advantageously the needle tip is provided with an asymmetric multi-plane mouth not angled in the same direction, and offset from the needle axis. A key feature being asymmetry of the relative mouth planes (direction and offset). Preferably the anterior lip of the tip mouth is chamfered in one direction with respect to the tip axis. Advantageously the posterior lip is chamfered in two directions with respect to the tip axis so as to form a triple chamfered tip mouth.

In one embodiment the posterior lip is curved outwards away from the tip axis. In another embodiment the posterior lip is curved inwards towards the needle axis. In a further embodiment the posterior lip is formed with multiple in-curves or crenations. Advantageously the lip edge curves are not formed around the full circumference of the mouth and are placed asymmetrically in one or more planes about the tip mouth.

In a still further embodiment the anterior lip is curved inwards so as to form a "kidney-shaped" tip mouth. Preferably the posterior lip is angled with respect to the tip axis so as to form an acute angle. Advantageously the anterior lip is formed with a plurality of serrations. These serrations need not be symmetric around the full circumference of the mouth. Preferably the serrations are placed in one plane or another, asymmetrically with respect to the major axis of the tip mouth.

According to another aspect of the present invention there is provided a needle for a surgical instrument for removal of diseased or unwanted tissue, the needle comprising:

a hollow elongate needle shaft having a needle tip at a distal end for cutting tissue, the needle tip being flared in at least one plane and having a flattened posterior lip and a curved anterior lip to produce a substantially D-shaped tip mouth with a major axis larger than an outer diameter of the needle shaft and a minor axis smaller than the major axis.

Typically the flattened posterior lip is on an edge of a posterior surface that lies in a plane that is substantially parallel to a central longitudinal axis of the needle shaft. Preferably the needle tip has a central longitudinal axis (the tip axis) which is substantially parallel to the central longitudinal axis of the needle shaft. In one embodiment the anterior lip of the tip mouth is also flattened and is on the edge of an anterior surface that lies in a plane that is substantially parallel to a central longitudinal axis of the needle shaft. Advantageously the amount of flattening of lip of the tip mouth is asymmetric around the mouth circumference.

Preferably the substantially D-shaped tip mouth lies in a plane that is substantially orthogonal to a central longitudinal axis (the needle axis) of the needle shaft. Advantageously the posterior lip is substantially transverse to the minor axis of the tip mouth and is on the edge of the posterior surface which is substantially parallel to the major axis of the tip mouth.

According to a further aspect of the present invention there is provided a needle for a surgical instrument for removal of diseased or unwanted tissue, the needle comprising:

a hollow elongate needle shaft having a needle tip at a distal end for cutting tissue, the needle tip having a mouth with a lip that has at least one in-curve formed in the lip to increase the lip surface area per length of circumference of the mouth of the needle tip.

According to a still further aspect of the present invention there is provided a needle for a surgical instrument for removal of diseased or unwanted tissue, the needle comprising:

a hollow elongate needle shaft having a needle tip at a distal end for cutting tissue, the needle tip having a mouth with a lip and a plurality of serrations provided on the lip to improve the cutting action of the needle tip.

According to yet another aspect of the present invention there is provided a needle for a surgical instrument for removal of diseased or unwanted tissue, the needle comprising:

a hollow elongate needle shaft having a needle tip at a distal end for cutting tissue, the needle tip having a mouth with a lip and wherein at least a portion of the lip is curved inwards so as to form a "kidney-shaped" tip mouth.

Throughout the specification, unless the context requires otherwise, the word "comprise" or variations such as "comprises" or "comprising", will be understood to imply the inclusion of a stated integer or group of integers but not the exclusion of any other integer or group of integers. Likewise the word "preferably" or variations such as "preferred", will be understood to imply that a stated integer or group of integers is desirable but not essential to the working of the invention.

BRIEF DESCRIPTION OF THE DRAWINGS

The nature of the invention will be better understood from the following detailed description of several specific embodiments of a needle tip for a surgical instrument, given by way of example only, with reference to the accompanying drawings, in which:

FIG. 1(a) is a top plan view of the mouth at the end of a first embodiment of a needle tip in accordance with the present invention;

FIGS. 1(b) and (c) are anterior and side elevations respectively of the needle tip of FIG. 1(a);

FIGS. 1(d) and (e) are top oblique anterior and the posterior perspective views respectively of the needle tip of FIG. 1(a);

FIG. 2(a) is a top plan view of the mouth at the end of a second embodiment of a needle tip in accordance with the present invention;

FIGS. 2(b) and (c) are anterior and side elevations respectively of the needle tip of FIG. 2(a);

FIGS. 2(d) and (e) are top oblique anterior and the posterior perspective views respectively of the needle tip of FIG. 2(a);

FIG. 3(a) is a top plan view of the mouth at the end of a third embodiment of a needle tip in accordance with the present invention;

FIGS. 3(b) and (c) are anterior and side elevations respectively of the needle tip of FIG. 3(a);

FIGS. 3(d) and (e) are top oblique anterior and the posterior perspective views respectively of the needle tip of FIG. 3(a);

FIG. 4(a) is a top plan view of the mouth at the end of a fourth embodiment of a needle tip in accordance with the present invention;

FIGS. 4(b) and (c) are anterior and side elevations respectively of the needle tip of FIG. 4(a);

FIGS. 4(d) and (e) are tope oblique anterior and the posterior perspective views respectively of the needle tip of FIG. 4(a);

FIG. 5(a) is a top plan view of the mouth at the end of a fifth embodiment of a needle tip in accordance with the present invention;

FIGS. 5(b) and (c) are anterior and side elevations respectively of the needle tip of FIG. 5(a);

FIGS. 5(d) and (e) are top oblique perspective views respectively of the anterior and the posterior needle tip of FIG. 5(a);

FIG. 6(a) is a top plan view of the mouth at the end of a sixth embodiment of a needle tip in accordance with the present invention;

FIGS. 6(b) and (c) are anterior and side elevations respectively of the needle tip of FIG. 6(a);

FIGS. 6(d) and (e) are top oblique anterior and the posterior perspective views respectively of the needle tip of FIG. 6(a);

FIG. 7(a) is a top plan view of the mouth at the end of a seventh embodiment of a needle tip in accordance with the present invention;

FIGS. 7(b) and (c) are anterior and side elevations respectively of the needle tip of FIG. 7(a);

FIGS. 7(d) and (e) are top oblique perspective views respectively of the anterior and the posterior needle tip of FIG. 7(a);

FIG. 8(a) is a top plan view of the mouth at the end of a eighth embodiment of a needle tip in accordance with the present invention;

FIGS. 8(b) and (c) are anterior and side elevations respectively of the needle tip of FIG. 8(a);

FIGS. 8(d) and (e) are top oblique anterior and the posterior perspective views respectively of the needle tip of FIG. 8(a);

FIG. 9(*a*) is a top plan view of the mouth at the end of a ninth embodiment of a needle tip in accordance with the present invention;

FIGS. 9(*b*) and (*c*) are the anterior and side elevations respectively of the needle tip of FIG. 9(*a*);

FIGS. 9 (*d*) and (*e*) are top oblique anterior and the posterior perspective views respectively of the needle tip of FIG. 9(*a*);

FIG. 10(*a*) is a top plan view of the mouth at the end of a tenth embodiment of a needle tip in accordance with the present invention;

FIGS. 10(*b*) and (*c*), are anterior and side elevations respectively of the needle tip of FIG. 10(*a*);

FIGS. 10(*d*) and (*e*) are top oblique anterior and the posterior perspective views respectively of the needle tip of FIG. 10(*a*);

FIG. 11(*a*) is a top plan view of a eleventh embodiment of the mouth at the end of a needle tip in accordance with the present invention;

FIGS. 11(*b*) and (*c*) are anterior and side elevations respectively of the needle tip of FIG. 11(*a*); and, FIGS. 11(*d*) and (*e*) are top oblique anterior and the posterior perspective views respectively of the needle tip of FIG. 11(*a*).

DETAILED DESCRIPTION OF PREFERRED EMBODIMENTS

A first embodiment of a needle 10 for a surgical instrument for removal of diseased or unwanted tissue in accordance with the invention is illustrated in FIG. 1. The needle 10 comprises a hollow elongate needle shaft 12 having a needle tip 14 for cutting tissue at a distal end of the needle shaft 12. The needle tip 14 is flared in at least one plane and has a flattened posterior lip 16 and a curved anterior lip 18 to produce a substantially D-shaped tip mouth 20 in a plane that is substantially orthogonal to a central longitudinal axis C—O—C' (the needle axis) of the needle 10 (as shown in FIG. 1(*a*)). A major axis A-A' of the tip mouth 20 is larger than an outer diameter of the needle shaft 12 and a minor axis B—B' is smaller than the major axis A-A'. Both the major axis A-A' and minor axis B-B' are substantially orthogonal to the needle axis C—O—C', creating a forward facing mouth 20 at the distal end 14 of the needle shaft 12. The intersection of the major axis A-A' and the minor axis B—B' is slightly offset from the needle axis C—O—C'.

In this and all subsequent embodiments the flattened posterior lip 16 extends along the edge of a posterior surface 22 of the needle tip that lies in a plane that is substantially parallel to the needle axis C—O—C'. However, although preferable, this is by no means essential to the invention. For example, the flattened posterior lip 16 may extend along the edge of a posterior surface 22 of the needle tip 14 that lies in a plane that is angled with respect to the needle axis C—O—C'. Preferably the needle tip 14 has a central longitudinal axis (the tip axis, C—O) which is substantially parallel to a central longitudinal axis (the shaft axis O—C') of the needle shaft 12. In this embodiment (and all subsequently described embodiments) the tip axis C—O is substantially collinear with the shaft axis O—C', however this is not essential to the present invention. The tip axis C—O could be inclined with respect to the shaft axis O—C'.

In this first embodiment, the anterior lip 18 of the tip mouth 20 is also flattened and extends along the edge of an anterior surface 24 of the needle tip that lies in a plane that is substantially parallel to needle axis C—O—C'. As can be seen most clearly in FIG. 1(*c*) the posterior surface 22 and anterior surface 24 are substantially parallel. Hence in this embodiment the needle tip 14 is flared in only one plane, namely, a plane which is parallel to the major axis A=A' of the tip mouth 20 and the tip axis C—O, and preferably slightly offset from the needle axis C—O—C'.

Preferably the major axis A-A' of the tip mouth 20 is about 1.2 to 2.5 times longer than the minor axis B—B'. Preferably the minor axis of the tip mouth 20 is about 1.0 to 1.5 times the diameter of the needle shaft.

Throughout this specification the term "posterior" refers to the lip, or surface, or edge that is situated at the back of the needle tip, or most distant in the surgeon's line of sight, when viewed in normal operation. In other words the posterior lip (lip 16 in FIG. 1) is generally the leading edge of the needle tip, which first enters the tissue of the eye. The term "anterior" thus refers to the opposite lip or surface, namely that which is situated on the front of the needle tip, or nearest in the surgeon's line of sight, when viewed in normal operation. In other words the anterior lip (lip 18 in FIG. 1) is generally the trailing edge of the needle tip, which last enters the tissue of the eye.

We have found that an optimal cutting effect for transverse or torsional needle tip movement can be achieved with one flattened edge—namely the leading edge or posterior lip of the tip mouth. Preferably at least a portion of the lip of the tip mouth is cut or chamfered at an angle with respect to the tip axis C—O. Preferably at least a portion of the lip of the tip mouth 20 is chamfered in a plane that is substantially parallel to the major axis A-A' of the tip mouth. A dual plane mouth (not angled in the same direction), offset from the needle axis C—O—C' is also optimal. A key feature being asymmetry of the relative, mouth planes (direction and offset). Combining the two features gives asymmetric flattening of the tip mouth—a flattened leading edge (posterior lip) and a curved trailing anterior lip, i.e. a "D-shaped" tip mouth when viewed in plan as shown in FIG. 1(*a*). The flattened leading edge of posterior lip 16 provides improved cutting efficiency, and the offset chamfer opens the face of the tip mouth more laterally so that during torsional movement aspiration flow is enhanced.

The asymmetry could apply to the use of serrations. A tip with serrations only on the lateral edges of the mouth tip was found to be more efficient on testing than just a plane lip. We found that addition, of a few such serrations produced up to four times more cutting effect than with a plain lip (milligrams cut per effective torsional ultrasound second increased from 0.69 to 2.73 with the addition of asymmetric serrations—see Table 5 below).

The asymmetry could also apply to grooves along part of the throat (say the posterior lip throat) but not elsewhere.

In the embodiment of FIG. 1 the anterior lip 18 of the tip mouth is chamfered in one direction with respect to the tip axis C—O. In other words, the anterior surface 24 of the needle tip 14 has been cut obliquely relative to the tip axis C—O so that the anterior lip 18 lies in a plane that is oblique to the tip axis C—O and substantially parallel to the major axis A-A' of the tip mouth, as can be seen most clearly in FIG. 1(*c*). By contrast, the posterior lip 16 lies in a plane that is substantially perpendicular to the tip axis C—O. This has the effect of not only providing better visualisation of the leading edge 18 for the surgeon, but increases the area of the tip mouth 20 to provide better grip with vacuum. It also opens up the anterior face of the needle (especially laterally) to improve the flow of aspiration into the mouth 20 as the needle rotates back and forth about the needle axis C—O—C'.

A second embodiment of a needle 30 for a surgical instrument for removal of diseased or unwanted tissue in accordance with the invention is illustrated in FIG. 2. The needle 30 is similar to the first embodiment of FIG. 1, and therefore the similar parts will be identified using the same reference numerals, and will not be described again in detail. The principal difference in the needle 30 is that an anterior surface 36 is flared so that the anterior lip 32 of the needle tip 34 is more rounded than the anterior lip 18 of the needle 10. In this embodiment the anterior lip 32 extends along the leading edge of anterior surface 36 which is flared relative to the longitudinal axis C—O—C' of the needle 10, as can be seen most clearly in FIG. 2(c). This asymmetric flare produces a further increase in mouth area, providing a better grip on the tissue when vacuum with aspiration is applied. In other respects the needle 30 is substantially identical to the needle 10.

A third embodiment of a needle 40 for a surgical instrument for removal of diseased or unwanted tissue in accordance with the invention is illustrated in FIG. 3. The needle 40 is similar to the second embodiment of FIG. 2, and therefore the similar parts will be identified using the same reference numerals, and will not be described again in detail. However, in this embodiment a posterior lip 42 of the needle tip 44 is chamfered with respect to the tip axis C—O in two directions along the major axis A-A' so as to form a blunt point, as can be seen most clearly in FIG. 3(b). The two chamfers on the posterior lip 42 lie in respective planes that are both parallel to the minor axis B—B'. The point at which the two chamfered edges of the posterior lip 42 meet lies on the minor axis B—B' of the tip mouth. As with the previous two embodiments, the anterior lip 32 of the tip mouth 20 is chamfered in one direction with respect to the tip axis C—O, in a plane that lies substantially parallel to the major axis A-A' of the tip mouth, so as to form a triple chamfered tip mouth.

A fourth embodiment of a needle 46 in accordance with the invention, as illustrated in FIG. 4, is substantially identical to the needle 40 except that the blunt point on the posterior lip 42 of the needle tip 48 has been radiused (rounded) to form a smooth transition between the chamfered edges of the posterior lip 42.

A fifth embodiment of a needle 50 for a surgical instrument for removal of diseased or unwanted tissue in accordance with the invention is illustrated in FIG. 5. The needle 50 is similar to the needle 30 of FIG. 2, and therefore the similar parts will be identified using the same reference numerals, and will not be described again in detail. However, in this embodiment a posterior lip 52 of the needle tip 54 is formed with multiple in-curves or crenations 56. Like lip serrations, the crenations 56 increase the surface area and the amount of cutting edge on the posterior lip 52 per effective tip mouth circumference. In the illustrated embodiment the posterior lip 52 is provided with three crenations 56 to form a wavy posterior surface at the lip edge. This enhances the effect of transversal or torsional motion at the lip of the tip mouth, and disperses the ultrasonic energy in a different pattern to improve emulsification.

A sixth embodiment of a needle 60 for a surgical instrument for removal of diseased or unwanted tissue in accordance with the invention is illustrated in FIG. 6. The needle 60 is similar to the needle 50 of FIG. 5, and therefore the similar parts will be identified using the same reference numerals, and will not be described again in detail. However, in this embodiment a posterior lip 62 of the needle tip 64 is formed with a single shallow in-curve or crenation 66.

A seventh embodiment of a needle 70 for a surgical instrument for removal of diseased or unwanted tissue in accordance with the invention is illustrated in FIG. 7. The needle 70 is similar to the needle 40 of FIG. 3, and therefore the similar parts will be identified using the same reference numerals, and will not be described again in detail. As with the needle 40 of FIG. 3, the posterior lip 72 of the needle tip 74 is chamfered in two directions with respect to the tip axis C—O so as to form a triple chamfered tip mouth. However, in this embodiment the posterior lip 72 is formed with a lip out-curl 76, as can be seen most clearly in FIG. 7(c). The point at which the two chamfered edges of the posterior lip 72 meet is curled outwards to enhance the cutting efficiency.

An eighth embodiment of a needle 80 for a surgical instrument for removal of diseased or unwanted tissue in accordance with the invention is illustrated in FIG. 8. The needle 80 is similar to the needle 30 of FIG. 2, and therefore the similar parts will be identified using the same reference numerals, and will not be described again in detail. In this embodiment, in addition to the flattened posterior lip 82, the needle tip 84 also has a multi-deformed anterior surface 86 with serrated anterior lip 88. As can be seen most clearly in FIG. 8(c), the anterior surface 86 is flared outwards, but then is flattened about half way along its length so as to curve inwards towards the posterior lip 82.

Furthermore, the anterior lip 88 is formed with a plurality of serrations 85 that are curled inwards into the mouth of the tip 84. The serrations 85 enhance the cutting efficiency of the tip, particularly for lateral and elliptical tip motion. By extending into the mouth of the needle tip 84 the serrations help to prevent blockage of the tip throat by further cutting-up larger pieces of lens material. Multiple crenations could also be used on the anterior lip 88 to achieve a similar effect. As can be seen most clearly in FIG. 8(c), the posterior lip 82 is partly chamfered with respect to the tip axis C—O, a second chamfer at a different angle forms a distinct anterior lip that together the two chamfers forms an acute angle at the lateral edge of the mouth. The in-curl of the anterior lip 88 places it at approximately the same angle as the chamfer of the posterior lip 82. This angles the anterior lip or trailing edge appropriately to aid the insertion of the needle into the wound.

A ninth embodiment of a needle 90 in accordance with the invention, as illustrated in FIG. 9, is similar to the needle 80 of FIG. 8, and therefore the similar parts will be identified using the same reference numerals, and will not be described again in detail. The main difference in the needle 90 is that the serrations 95 on the anterior lip 98 of the needle tip 94 are less evenly curled inwards, creating a pronounced saw tooth pattern compared to the embodiment of FIG. 8 due to the different deformation of the anterior surface 96. This creates an improved cutting effect with the serrations further enhancing efficiency. In this embodiment the anterior surface 96 is also flared outwards, but the flattening or in-curl of the anterior surface 96 occurs about two thirds of the way along its length so as to curve inwards towards the posterior lip 92.

A tenth embodiment of a needle 100 in accordance with the invention, as illustrated in FIG. 10, is similar to the needle 90 of FIG. 9, and therefore the similar parts will be identified using the same reference numerals, and will not be described again in detail. The main difference in the needle 100 is the absence of any serrations on the anterior lip 108 of the needle tip 104. In this embodiment the anterior surface 106 has an in-curl similar to the anterior surface 96 of FIG. 9; however the anterior lip 108 itself is smooth with a more or less straight edge.

An eleventh embodiment of a needle 110 in accordance with the invention, as illustrated in FIG. 11, is similar to the needle 100 of FIG. 10, and therefore the similar parts will be identified using the same reference numerals, and will not be described again in detail. In fact the main difference between this embodiment and the previous one is the angle of the chamfer on the posterior lip 112. The chamfer on the posterior lip 112 in this embodiment is more acute, and the anterior surface 116 is slightly longer so that the anterior lip 118 extends almost as far as the posterior lip 112. Also the in-curled portion of the anterior surface 118 is not curled in as much as the previous embodiment.

Producing a dual (or multi) plane tip mouth with two lips may create difficulties in passing through the wound, as the trailing edge (anterior lip) may catch. Curling inwards of the anterior lip not only allows for better surgical ergonomics, it concentrates the cutting effect closer to the needle axis providing a different dispersal of ultrasound energy within the tip mouth and throat 20, whilst allowing good flow of aspiration around the lateral lip. The result, as is apparent from FIGS. 8 to 11, is a "kidney shaped" tip mouth.

Multiple smaller lip in-curls or longer in-curves may be useful, particularly in asymmetric configurations. The effect is to extend the creases so produced down the throat and around the lip dispersing the ultrasonic energy within the mouth in a more turbulent way enhancing the emulsification effect. Crenations and lip curl effects may be usefully combined with lip serrations and throat grooves to further enhance the cutting efficiency.

Bench Test Data

A specially designed test chamber was built to enable gentle application of composite wax samples to the mouth of the phaco probe needle tip at 0.045N force during emulsification and aspiration. The wax samples were prepared as a 6×6 mm cylinder, weighed before mounting, and during testing were cut through four times by the needle. The samples were reweighed to determine the weight of the material removed by the cuts.

The phaco machine parameters were kept constant for all cuts and the foot pedal was at full excursion for the entire duration of the cut. Torsional power was set at 100%, vacuum was limited to 250 mmHg, aspiration rate was set to 35 mL/min, the infusion height was at 110 cm for all cuts.

The four cuts were replicated seven times for both the Kelman 45° needle and a Flattened tip prototype. The ultrasound time and percent power from the phaco machine's metrics screen were recorded for the cuts, and multiplied to produce the "effective" ultrasound time. The vacuum, aspiration and motion of the material over the tip and needle were measured independently from the machine by the test rig and logged continuously throughout the cut.

The total time for the cut, and the time to peak vacuum were determined from the independent data-log and used to derive the parameters shown in the results tables below.

Averages and 95% confidence intervals were determined for each of the parameters.

TABLE 1

| Cutting Efficiency | Kelman | | Flattened | |
|---|---|---|---|---|
| | avg | ±95% CI | avg | ±95% CI |
| mg cut | 7.00 | 2.27 | 13.29 | 3.98 |
| effective US time | 27.88 | 7.66 | 12.68 | 2.80 |
| mg cut per effective US time | 0.33 | 0.22 | 1.25 | 0.62 |
| Mm cut per sec | 1.00 | 0.32 | 2.07 | 0.52 |

The Flattened tip required half as much torsional ultrasound power to cut twice as much material compared to the Kelman tip. The tip configuration thus made a considerable difference in the application of torsional ultrasound energy to the test material. The rate of cut was twice as fast as a result of this significant improvement in cutting efficiency.

TABLE 2

| Fluidics Efficiency | Kelman | | Flattened | |
|---|---|---|---|---|
| | avg | ±95% CI | avg | ±95% CI |
| Time to peak vac | 1.74 | 0.21 | 1.86 | 0.22 |
| mg cut to peak vac | 0.46 | 0.22 | 1.54 | 0.67 |
| mm cut to peak vac | 0.95 | 0.39 | 1.79 | 0.83 |
| mL aspirated to peak vac | 0.45 | 0.14 | 0.38 | 0.16 |
| % of cut time at max vac | 75.47% | 5.74% | 55.73% | 9.41% |
| mg cut per mL aspirate | 1.38 | 0.58 | 5.55 | 2.93 |
| mL aspirated per US time | 0.12 | 0.05 | 0.16 | 0.06 |

Although both needles reach peak vacuum at the same time and aspirate at the same rate, the Flattened tip utilizes flow and, in particular, vacuum more efficiently. Once at peak vacuum, the Flattened tip cut rate accelerates, so the amount cut per mL of flow is significantly increased. This enables the Flattened tip needle to complete the cut in half the time of the Kelman needle.

TABLE 3

| Temperature Efficiency | Kelman | | Flattened | |
|---|---|---|---|---|
| | avg | ±95% CI | avg | ±95% CI |
| Increase in shaft temp (° C.) | 1.84 | 0.71 | 0.01 | 0.02 |

The temperature of the needle shaft of the Kelman needle increased significantly during the cuts (the tip was "loaded" with the test material), whereas there was no temperature change seen in the Flattened tip needle. This reflects the inefficiency of the cutting action of the Kelman needle.

In a separate configuration of the test chamber, thermocouples measured the base of the needle shaft and just behind the tip (at the beginning of the flare or angle of the bend) with the needle's infusion sleeve in place covering the needle shaft. 100% torsional power was applied for one minute and the peak temperature recorded. Tests were performed with a high flow, a low flow, and chamber full of dispersive viscoelastic with a low flow, each time the needle tip was "unloaded".

TABLE 4

| | Increase in needle shaft temp (° C.) sleeved needle | | | | | |
|---|---|---|---|---|---|---|
| | base of needle | | % difference | distal needle | | % difference |
| | Flattened | Kelman | | Flattened | Kelman | |
| High flow | 20.8 | 25.9 | −20% | 22.8 | 22.1 | 3.2% |
| Low flow | 24.0 | 25.9 | −7.3% | 22.8 | 25.3 | −9.9% |
| Viscoelastic | 38.0 | 41.0 | −7.3% | 40.0 | 40.5 | −1.2% |
| Avg | | | −11% | | | −3% |

The needle's irrigation sleeve substantially cools the Flattened tip needle shaft base but not the Kelman needle shaft base. This suggests that the Kelman needle temp is not only affected by the hand-piece piezo-electric crystals generating heat, but also by the needle motion itself. Again this reflects the inefficiency of the Kelman needle action.

Additional tests were also conducted to measure any improvement in cutting efficiency using a flattened tip mouth with asymmetric serrations on the lip, relative to a flattened tip mouth without serrations. As can be seen from Table 5 below, the addition of serrations on one of the flattened lip portions (anterior or posterior) to produce asymmetric serrations resulted in an almost fourfold increase in cutting efficiency, measured as the weight of material cut (mg) per the effective ultrasonic (US) time.

TABLE 5

Cutting efficiency of tip edge configuration

|  | flattened only | | flattened with asymmetric serrations | |
| --- | --- | --- | --- | --- |
|  | avg | sd | avg | sd |
| cut weight (mg) | 1.41 | 1.54 | 4.99 | 2.61 |
| effective US time | 2.03 | 0.56 | 1.83 | 0.99 |
| mg cut per effective US time | 0.69 | 2.76 | 2.73 | 2.64 |

Now that several embodiments of the surgical needle tip have been described in detail, it will be apparent that the embodiments provide a number of advantages over the prior art, including the following:
 (i) Improved efficiency in cataract removal compared with a conventional tip (as less energy is put into the eye for phacoemulsification because of better cutting action).
 (ii) Less disruption during the procedure due to tip blockage.
 (iii) The tip design on a straight needle reduces any thermal side effects of the needle shaft in the wound during phacoemulsification (reduced risk of wound damage).
 (iv) Enhanced fluidics by opening the lateral tip mouth to promote flow, and enlarging the tip mouth area to provide better grip with vacuum.
 (v) Good visualisation of the tip mouth and instrument handling ergonomics for the surgeon performing the phacoemulsification procedure.

It will be readily apparent to persons skilled in the relevant arts that various modifications and improvements may be made to the foregoing embodiments, in addition to those already described, without departing from the basic inventive concepts of the present invention. For example, in all of the above described embodiments the crenations and lip curl effects are combined with a D-shaped tip mouth. However the crenations and lip curl effects may also be combined with any other shaped needle tip to provide improved cutting efficiencies. Therefore, it will be appreciated that the scope of the invention is not limited to the specific embodiments described.

The invention claimed is:

1. A needle for a surgical instrument for removal of diseased or unwanted tissue, the needle comprising:
 a hollow elongate needle shaft having a needle tip at a distal end for cutting tissue, the needle tip being flared in at least one plane and having a posterior lip on an edge of a posterior surface and an anterior lip on an edge of an anterior surface, the posterior lip and the anterior lip intersect one another at first and second intersection points;
 in an end plan view the posterior lip is flattened and the anterior lip is continuously curved from the first intersection point to the second intersection point to produce an asymmetric tip mouth with a major axis and a minor axis, the major axis being substantially parallel to the posterior lip, a total width of the tip mouth on the major axis being larger than an outer diameter of the needle shaft and a total height of the tip mouth on the minor axis being smaller than the total width, and wherein the posterior lip is substantially transverse to the minor axis; and
 in side elevation view at least a portion of the anterior lip of the tip mouth is cut or chamfered in one direction with respect to a central longitudinal axis of the needle tip and at least a portion of the posterior lip of the tip mouth is cut or chamfered in a different direction with respect to the central longitudinal axis of the needle tip so as to form a multi-plane tip mouth which opens the face of the tip mouth more laterally wherein, in use, during torsional movement of the needle tip aspiration flow is enhanced and better visualization of the posterior lip is provided for a surgeon.

2. A needle for a surgical instrument as defined in claim 1, wherein the tip mouth is substantially D-shaped.

3. A needle for a surgical instrument as defined in claim 2, wherein in side elevation view the posterior surface lies in a plane that is substantially parallel to a central longitudinal axis of the needle shaft.

4. A needle for a surgical instrument as defined in claim 3, wherein the posterior lip is substantially parallel to the major axis of the tip mouth.

5. A needle for a surgical instrument as defined in claim 3, wherein the posterior lip is curved inwards towards the central longitudinal axis of the needle shaft.

6. A needle for a surgical instrument as defined in claim 5, wherein the posterior lip is formed with multiple in-curves or crenations.

7. A needle for a surgical instrument as defined in claim 6, wherein the lip edge in-curves are not formed around a full circumference of the tip mouth and are placed asymmetrically in one or more planes about the tip mouth.

8. A needle for a surgical instrument as defined in claim 2, wherein in side elevation view the anterior surface lies in a plane that is substantially parallel to a central longitudinal axis of the needle shaft.

9. A needle for a surgical instrument as defined in claim 8, wherein the anterior lip and the posterior lip of the tip mouth are asymmetric about the major axis.

10. A needle for a surgical instrument as defined in claim 1, wherein the central longitudinal axis of the needle tip is substantially parallel to a central longitudinal axis of the needle shaft.

11. A needle for a surgical instrument as defined in claim 10, wherein the tip mouth lies in a plane that is substantially orthogonal to the central longitudinal axis of the needle shaft.

12. A needle for a surgical instrument as defined in claim 10, wherein the posterior lip is curved outwards away from the central longitudinal axis of the needle tip.

13. A needle for a surgical instrument as defined in claim 1, wherein the major axis of the tip mouth is about 1.2 to 2.5 times longer than the minor axis.

14. A needle for a surgical instrument as defined in claim 13, wherein the minor axis is about 1.0 to 1.5 times a diameter of the needle shaft.

15. A needle for a surgical instrument as defined in claim 1, wherein in side elevation view at least a portion of the anterior lip of the tip mouth is chamfered in a plane that is substantially parallel to the major axis of the tip mouth.

16. A needle for a surgical instrument as defined in claim 14, wherein the posterior lip is chamfered in two directions with respect to the central longitudinal axis of the needle tip so as to form a triple chamfered tip mouth.

17. A needle for a surgical instrument as defined in claim 1, wherein an intersection of the major axis and the minor axis is offset from a central longitudinal axis of the needle shaft, and the intersection is positioned closer to the posterior lip than to an apex of the anterior lip.

18. A needle for a surgical instrument for removal of diseased or unwanted tissue, the needle comprising:
   a hollow elongate needle shaft having a needle tip at a distal end for cutting tissue, the needle tip being flared in at least one plane and having a flattened posterior lip on an edge of a posterior surface and an anterior lip on an edge of an anterior surface; in an end plan view the anterior lip has no flattened portions to produce a substantially D-shaped tip mouth, and a total width of the tip mouth on a major axis being larger than an outer diameter of the needle shaft and a total height of the tip mouth on a minor axis being smaller than the total width, and wherein the posterior lip is substantially transverse to the minor axis; and
   in side elevation view at least a portion of the anterior lip of the tip mouth is cut or chamfered in one direction with respect to a central longitudinal axis of the needle tip and at least a portion of the posterior lip of the tip mouth is cut or chamfered in a different direction with respect to the central longitudinal axis of the needle tip so as to form a multi-plane tip mouth which opens the face of the tip mouth more laterally wherein, in use, during torsional movement of the needle tip aspiration flow is enhanced and better visualization of the posterior lip is provided for a surgeon.

19. A needle for a surgical instrument as defined in claim 18, wherein in side elevation view the posterior surface lies in a plane that is substantially parallel to a central longitudinal axis of the needle shaft.

20. A needle for a surgical instrument as defined in claim 19, wherein the posterior surface is substantially parallel to the major axis of the tip mouth.

21. A needle for a surgical instrument as defined in claim 18, wherein the central longitudinal axis of the needle tip is substantially parallel to a central longitudinal axis of the needle shaft.

22. A needle for a surgical instrument as defined in claim 18, wherein in side elevation view the anterior surface lies in a plane that is substantially parallel to a central longitudinal axis of the needle shaft.

23. A needle for a surgical instrument as defined in claim 22, wherein the anterior lip and the posterior lip of the tip mouth are asymmetric about the major axis.

24. A needle for a surgical instrument as defined in claim 18, wherein the substantially D-shaped tip mouth lies in a plane that is substantially orthogonal to a central longitudinal axis of the needle shaft.

* * * * *